United States Patent [19]

Zupancic et al.

[11] Patent Number: 4,728,708
[45] Date of Patent: Mar. 1, 1988

[54] THERMOSET POLYMERS OF STYRENE TERMINATED TETRAKIS PHENOLS

[75] Inventors: Joseph J. Zupancic, Bensenville; Andrew M. Zweig, Streamwood; James A. Wrezel, Buffalo Grove, all of Ill.

[73] Assignee: Allied Corporation, Morris Township, Morris County, N.J.

[21] Appl. No.: 947,007

[22] Filed: Dec. 29, 1986

[51] Int. Cl.$^4$ .................. C08F 279/00; C08F 112/16; C08F 212/16
[52] U.S. Cl. ..................................... 526/293; 526/313
[58] Field of Search ......................... 526/313

[56] References Cited

U.S. PATENT DOCUMENTS 4,116,936 9/1978 Steiner ............................. 526/286

Primary Examiner—Peter F. Kulkosky
Attorney, Agent, or Firm—Harold N. Wells; Jay P. Friedenson

[57] ABSTRACT

Thermoset polymers of styrene terminated tetrakis phenols may be prepared from resins which possess the generic formula

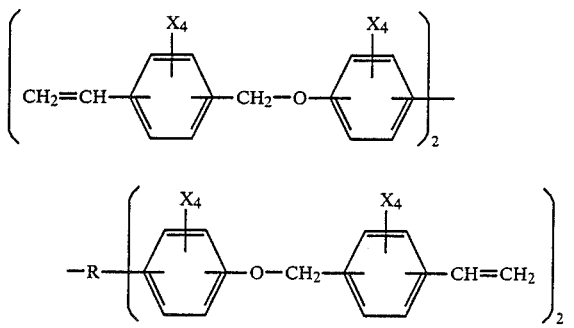

in which R is selected from the group consisting of alkyl, cycloalkyl, alkaryl and substituted alkaryl radicals and X is independently selected from the group consisting of hydrogen and halogen atoms. These polymers will be utilized as a component in laminates on circuit boards which are employed in relatively complicated pieces of electronic equipment.

10 Claims, No Drawings

THERMOSET POLYMERS OF STYRENE TERMINATED TETRAKIS PHENOLS

BACKGROUND OF THE INVENTION

With the advent of sophisticated equipment in the electrical and electronic fields, it has become necessary that the components of the various pieces of equipment conform to high standards which are set forth in the specifications for these components. For example, circuit boards which are used in relatively complicated pieces of equipment, such as main frame computers, must be of a relatively high standard of quality in order to function in an efficient manner for a long period of time without deteriorating or breaking down, and thus causing an interruption in the function of the machine. This high quality of material is opposed to pieces of equipment requiring a lower standard of quality such as those used in personal computers, high quality television equipment, radios, etc.

Circuit boards upon which a circuit is etched or implanted usually comprise a laminate which is composed of a synthetic polymeric substance which possesses desirable characteristics such as thermal stability, low coefficient of thermal expansion, dimensional stability, low dielectric constant, solvent resistance, low moisture absorption, etc., and a suitable reinforcement matrix, such as glass, quartz, graphite, Kevlar, etc.

As will hereinafter be shown, it has now been discovered of that certain thermoset polymers of polyvinyl benzyl ethers) of polyphenols may be utilized as a component in the preparation of laminates which themselves will form a component of a circuit board and will possess the desirable characteristics hereinbefore set forth. The aforesaid thermoset polymers are derived or prepared from materials which comprise poly(vinyl benzyl ethers) of polyphenols having certain configuration. Alternatively, these compounds may also be designated as styrene terminated tetrakis phenols. The compounds which are used to form the polymers of the present invention differ from those which are described in U.S. Pat. No. 4,116,936 in that the compounds of the patent are bifunctional in nature in contrast to the compounds of the present invention which may be designated as multi- or polyfunctional in nature and which possess four or more functionalities.

By utilizing polymers which are obtained from the compounds of the present invention, it is possible for the users to avail themselves of certain advantages which are inherent between these compounds and the compounds described in U.S. Pat. No. 4,116,936. For example, the styrenated materials formed from the polyphenols of the present invention are non-crystalline in nature and possess a better solubility in resin formulations in both the A and B stage. Therefore, the polymers will stay in solution in the resultant formulation and crystallize out on standing. In addition, the polymers of the present invention will form excellent films during the B stage processing of the resin formulation and will be less likely to be brittle or flake off of the reinforcement upon which the formulation is impregnated.

BRIEF SUMMARY OF THE INVENTION

This invention relates to thermoset polymers which are prepared from resins of poly(vinyl benzyl ethers) of polyphenols having a specific structure. The thermoset polymers of the present invention, which constitute novel compositions of matter, may be used to coat and/or impregnate a substrate which is thereafter cured and utilized in circuit board laminates and dielectric coatings, the use thereof being attributable to the desirable characteristics which are possessed by these polymeric compositions of matter. The particular characteristics of the polymer dielectric and reinforcing components which go to make up the circuit boards contribute to the efficiency and stability of the final electronic equipment in which the circuit boards are used. For example, a lowering of the dielectric constant in the polymer matrix reduces the signal propagation delay or "crosstalk" and line capacitance. This results in faster PWB circuitry and, in addition, provides the potential to increase the number of functions per board. The polymeric matrix of the present invention possesses a lower dielectric constant than that which is possessed by thermosetting polyimide or epoxy matrices which are used as the standards by the industry for electrical laminates.

Another desirable characteristic of a polymer matrix for use in circuit boards is that the coefficient of thermal expansion should be relatively low in order to avoid a mismatch of thermal expansions with the electronic components and the fiberglass reinforcement with which the polymeric matrix is composited. The coefficient of thermal expansion of the novel thermoset polymers of the present invention may be comparable to a polyimide matrix. Furthermore, the thermal stability of the polymer matrix must be relatively high in nature inasmuch as the matrix must possess the ability to withstand soldering temperatures without melting or degrading. A desirable characteristic of the thermoset polymer of the present invention is that the thermal stability of the polymer is comparable to a polyimide matrix.

It is therefore an object of this invention to provide novel thermoset polymers.

Another object of this invention is to provide a method for preparing these thermoset polymers which will meet the requirement for chip encapsulation and potting materials and will also be useful as components in the formulation of circuit board laminates.

In one aspect, an embodiment of this invention resides in a thermoset polymer of a resin which comprises a poly(vinyl benzyl ether) of a polyphenol having the generic formula:

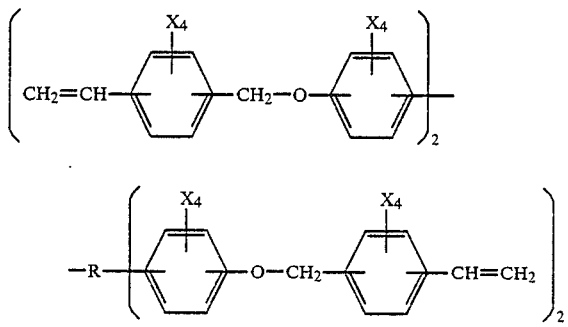

in which R is selected from the group consisting of alkyl, cycloalkyl, alkaryl and substituted alkaryl radicals and X is independently selected from the group consisting of hydrogen and halogen atoms. Other objects and embodiments will be found in the following further detailed description of this invention.

DETAILED DESCRIPTION OF THE INVENTION

As hereinbefore set forth, the present invention is concerned with novel thermoset polymers and to a method for the preparation of these polymers. The thermoset polymers are prepared from poly(vinyl benzyl ethers) of polyphenols and particularly styrene terminated tetrakis phenols. The cured polymer which is obtained from this material will be useful in electronic circuitry inasmuch as the final, crosslinked polymer will possess relatively low dielectric constants, high glass transition temperatures and suitable flow viscosity. These polymers are excellent candidates for continuous lamination, reinforced reaction injection molding, composite reaction injection molding or resin transfer molding applications.

The poly(vinyl benzyl ether) of a polyphenol which comprises the resin from which the desired thermoset polymer is obtained will possess the generic formula:

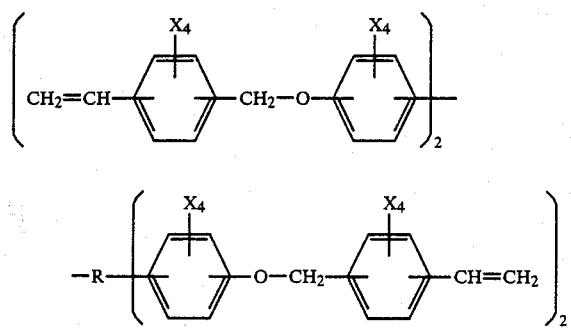

in which R is selected from the group consisting of alkyl, cycloalkyl, alkaryl and substituted alkaryl radicals and X is independently selected from the group consisting of hydrogen and halogen atoms.

In the preferred embodiment of the invention, the alkyl radical will contain from about 2 to about 6 carbon atoms and the cycloalkyl radical will contain from about 4 to about 12 carbon atoms.

The desired resins may be prepared by reacting a tetraphenol alkane, tetraphenol aromatic, tetraphenol cycloalkane or a tetraphenol substituted cycloalkane compound with a vinyl benzyl halide such as vinyl benzyl chloride at reaction conditions to form the desired product, namely a styrene-terminated-tetrakis phenol. The reaction conditions which are employed to effect the desired condensation will include temperatures ranging from about 60° to about 70° C. and preferably the reflux temperature for a period of time which may range from about 1 to about 4 hours in duration. After maintaining the reaction mixture at the desired temperature, a basic solution in an alcoholic medium may then be added and reflux continued. Upon completion of the desired reaction time, the reaction mixture may then be diluted with an organic solvent and allowed to remain at ambient temperature for a second predetermined period of time. Following this, the reaction mixture may be recovered and the desired product separated by conventional means from any unreacted starting material solvent, etc. to form the desired monomer.

Specific examples of tetraphenol compounds which may be employed as starting materials and condensed with the vinyl benzyl halide such as vinyl benzyl chloride may include
1,1,2,2-tetrakis(hydroxyphenyl)ethane;
1,1,3,3-tetrakis(hydroxyphenyl)propane;
1,1,4,4-tetrakis(hydroxyphenyl)butane;
1,1,5,5-tetrakis(hydroxyphenyl)pentane;
1,1,6,6-tetrakis(hydroxyphenyl)hexane;
1,1,3,3-tetrakis(hydroxyphenyl)cyclobutane;
1,1,3,3-tetrakis(hydroxyphenyl)cyclopentane;
1,1,4,4-tetrakis(hydroxyphenyl)cyclohexane;
1,1,4,4-tetrakis(hydroxyphenyl)cyclooctane;
1,1,5,5-tetrakis(hydroxyphenyl)cyclooctane;
1,1,4,4-tetrakis(hydroxyphenyl)m-xylene;
1,1,4,4-tetrakis(hydroxyphenyl)p-xylene; etc., and oligomers of these compounds.

It is to be understood that the aforementioned tetraphenol compounds are only representative of the class of compounds which may be employed as one of the components in the formation of the poly(vinyl benzyl ether) of a polyphenol and that the present invention is not necessarily limited thereto.

The resins may then, if so desired, be cured by dissolving the compound in an appropriate solvent. The dissolved material may then be heated to remove a major portion of the solvent and thereafter cured at an elevated temperature in an appropriate apparatus such as an oven for a period of time sufficient to form the desired insoluble, crosslinked thermoset material.

It is also contemplated within the scope of this invention that the desired resins may be prepared in a continuous manner of operation. For example, the tetraphenol compound and the vinyl benzyl halide may be continuously charged either separately or in a premixed state to a reaction zone which is maintained at the proper operating conditions of temperature and pressure. The components which are charged to the reaction zone in an appropriate solvent are passed through this zone for a predetermined period of time sufficient to form the desired monomer. After passage through the zone, the reaction mixture is recovered as reactor effluent and the desired monomer separated from any unreacted starting materials by conventional means such as fractional distillation or reprecipitation, and recovered.

The thermoset polymers of the styrene terminated tetrakis phenols may then be utilized as components in forming a laminate. For example, the polymer which has been synthesized according to the process hereinbefore set forth may be used in a resin casting operation. For example, the cured polymer may be dissolved in a suitable solvent such as chloroform, acetone, toluene, benzene, xylene or in aprotic solvent such as dimethylformamide or N-methylpyrrolidone at ambient temperature. This solution may then be used to impregnate a suitable filler or reinforcement such as fiberglass, Kevlar, graphite, alumina, quartz, ceramic, etc. to form a laminate precursor or prepreg. The prepreg may be a single ply or a predetermined number of plies which may be pressed together, or in between cured laminates, to form the desired circuit board matrix.

It is also contemplated within the scope of this invention that the laminate may be prepared in a continuous manner of operation. When such a type of operation is employed, a substrate or reinforcement is passed through a zone containing the resin dissolved in a solvent. After passage through the zone, the impregnated reinforcement is withdrawn and continuously charged to a curing zone where it is subjected to temperatures sufficient to remove excess solvent and/or a partial cure by passage through this zone which is maintained at varying operating temperatures for a predetermined period of time. After passage through the zone, the resulting prepreg material is continuously withdrawn and passed to storage. The prepreg may then be layed up as sheets with or without a metal such as copper foil as an electrical or thermal conductor and pressed with predetermined number of sheets to form the desired laminate or circuit board matrix. Optionally, the laminate may then be post-cured in an appropriate apparatus such as an oven to fully cure the material such that optimized properties of interest will result. The metal-covered laminate or uncovered laminate may then be cut into desired sizes and utilized, as hereinbefore set forth, as a circuit board in various electric or electronic devices.

In addition to the aforementioned favorable characteristics which are possessed by the thermoset polymers of the present invention, another advantage in utilizing these polymers as components of a laminate is when employing a halogenated derivative of the poly(vinyl benzyl ether) of a polyphenol. The function of these halogenated derivatives, and especially the brominated or chlorinated derivatives, will be to introduce a desired property enhancement to the substrate or reinforcement in that the laminate may then meet certain flammability requirements such as set forth in UL 94 flammability tests.

The following examples are given for purposes of illustrating the novel thermoset polymers which have been obtained from resins of a poly(vinyl benzyl ether) of a polyphenol having the generic formula hereinbefore set forth and which will possess the aforementioned desired properties. However, it is to be understood that these examples are given merely for purposes of illustration, and that the present invention is not necessarily limited thereto.

EXAMPLE 1

In this example, 100 grams (0.142 mole) of commercial-grade 1,1,2,2-tetraphenol ethane and 166.54 grams (1.091 moles) of vinyl benzyl chloride (60/40 meta/para isomer ratio) were dissolved in 250 milliliters of acetone in a three neck-round bottom flask which was equipped with a condenser, addition funnel, thermometer, mechanical stirrer and nitrogen purge. The reaction mixture was then heated to reflux (65°–70° C. temperature) for a period of one hour, following which a solution of 67.5 grams (1.202 moles) of potassium hydroxide in 150 milliliters of methanol was added to the warm reaction mixture over an interval of 30 minutes with continuous stirring. The reaction mixture was maintained at reflux temperature for a period of 1 hour, thereafter diluted with 400 milliliters of acetone and was then stirred at ambient temperature for a period of 24 hours. The reaction mixture was recovered, dried over magnesium sulfate, filtered and concentrated under vacuum. The oil was then taken up in an equal volume of acetone and precipitated from the acetone solution by the addition of methanol. The resulting solid was vacuum dried at ambient temperature for a period of 24 hours to yield 87.0 grams of a yellow crystalline material having a melting point of 52° C.; a $M_n$ of 1.088K (number-average molecular weight), a $M_w$ of 5.080K (weight-average molecular weight) and R of 4.67 (dispersity index). In addition, the material had a viscosity of 50 cps (50% solids, dimethylformamide, 23° C. In addition, elemental analysis disclosed 84.40% carbon, 5.94% hydrogen and 8.81% oxygen.

EXAMPLE II

To form the desired crosslinked thermoset matrix, 2.00 grams of the styrene-terminated tetraphenol ethane prepared according to the above example was dissolved in 10 milliliters of chloroform and the sample was heated on a hot plate at a temperature of from 90° to 95° C. to remove a major portion of the solvent. The sample was then cured in an oven at a temperature of 120° C. for a period of 2 hours, followed by a 16-hour cure at 160° C. and a 2-hour cure at 200° C. Following this, the sample was then post-cured for a period of 1 hour at 225° C. and recovered.

The cured polymer was found to have a glass transition temperature (Tg) greater than 300° C., a coefficient of thermal expansivity from 25° to 260° C. of 42±6PPM/°C. The dielectric constant of the polymer at 0% relative humidity and at 23° C. was 2.89±0.12 while the dissipation factor at 1 MHz. and at 0% relative humidity was 0.006±0.001.

EXAMPLE III

To form a halogen substituted compound, 100.65 g (0.143 moles) of commercial-grade 1,1,2,2-tetraphenol ethane, 100 milliliters of carbon tetrachloride and 230 milliliters of methanol were placed in a 1,000 milliliter round bottom, three-necked flask. The flask was equipped with a coarse sparge tube, an addition funnel, condenser, stirring bar and oil bubbler outlet. Potassium bromide in an amount of 5.0 g (0.042 moles) were added to the flask which was then heated to a temperature of from 45° to 55° C. by means of a water bath and sparged with nitrogen for 20 minutes. Thereafter 103.5 milliliters (321.1 g, 2.01 moles) of bromine was added to the warmed reaction mixture with stirring during a period of 4 hours. At the end of this time, 200 milliliters of water was added to the reaction mixture and the volatile products were distilled off at atmospheric pressure. The remaining residue was taken up in 400 milliliters of methylene chloride and the organic phase was washed three times with 200 milliliters of water, the third wash being effected at a pH of 5. The organic phase was then washed twice with 200 milliliters of a 10% aqueous sodium bisulfite solution to remove any residual bromine which may still have been present. After the wash with the sodium bisulfite solution, the organic phase was again washed with 200 milliliters of water and dried over sodium sulfate. The methylene chloride was removed under vacuum to afford a burgundy-colored crystalline solid. Azeotropic drying with ethanol gave 152.23 g of polybromotetraphenol ethane. Elemental analysis of the product found C=34.19%, H=2.00%, Br=55.03% and O=8.86%.

The desired monomer was prepared by charging 49.89 g ($2.655 \times 10^{-2}$ moles) of the polybromotetraphenol ethane, 35.5 g ($2.325 \times 10^{-1}$ *moles*) *of vinyl benzyl chloride and* 197.5 milliliters of acetone to a 1 liter, 3 necked flask equipped with a condenser, addition funnel, thermometer, nitrogen purge and magnetic stirring bar. The solution was stirred for a period of 30 minutes at 25° C. and thereafter refluxed for a period of 1 hour. Following this, a solution of 12.51 g ($2.23 \times 10^{-1}$ moles) of potassium hydroxide in 30 milliliters of methanol was added to the reaction mixture during an interval of 30 minutes with continuous stirring. Upon completion of the addition of sodium hydroxide, the stirred mixture was refluxed for a period of 1 hour and thereafter stirred at ambient temperature for an additional period of 16 hours. The crude reaction mixture was dried over magnesium sulfate, filtered and concentrated under vacuum. The resulting crude oil was taken up in 60 milliliters of acetone and precipitated from the acetone solution by the addition of 3000 milliliters of methanol. The resin was vacuum dried at ambient temperature for a period of 16 hours to yield 12.74 g of a tan crystalline material comprising styrene terminated polybrominated tetraphenol ethane.

EXAMPLE IV

The desired crosslinked, thermoset matrix of the styrene terminated polybromotetraphenol ethane, prepared according to Example III above, was prepared by dissolving 2.00 g of the material in 10 milliliters of methylene chloride which was then heated on a hot plate at a temperature of from about 90° to about 95° C. to remove a major portion of the solvent. The sample was then cured in a manner similar to that set forth in Example II above by heating in an oven at 120° C. for 2 hours, followed by a 16 hour cure at a temperature of 160° and a 2 hour cure at 200° C. Post curing of the polymer was effected by treating the polymer for a period of 1 hour at a temperature of 225° C.

The cured polymer was found to have a glass transition temperature greater than 300° C. a coefficient of thermal expansivity from 25° to 260° C. of 50±4 ppm/° C. The dielectric constant of the polymer at 0% relative humidity and 50% relative humidity at 23° C. was 2.79±0.26 and 2.90±0.21, respectively, while the dissipation factor at 1 MHz and 0% and 50% relative humidity was 0.003±0.001 and 0.008±0.001, respectively.

EXAMPLE V

In a manner similar to that set forth in the above example, other tetraphenol compounds such as 1,1,3,3-tetraphenol propane; 1,1,6,6-tetraphenol hexane; tetraphenol cyclobutane; tetraphenol cyclohexane; and tetraphenol cycloheptane may be reacted with vinyl benzyl chloride to form the desired resin. The resin, after recovery from the reaction product, may then be cured by heat at temperatures ranging from 120° C. to 20° C. followed by a post curing at 225° C. to form the desired crosslinked thermoset polymer. This latter compound could also be generated in the presence of a suitable reinforcement to form a thermoset structural or electrical laminate or circuit board.

We claim as our Invention:

1. A thermoset polymer of a resin which comprises a poly(vinyl benzyl ether) of a polyphenol having the generic formula:

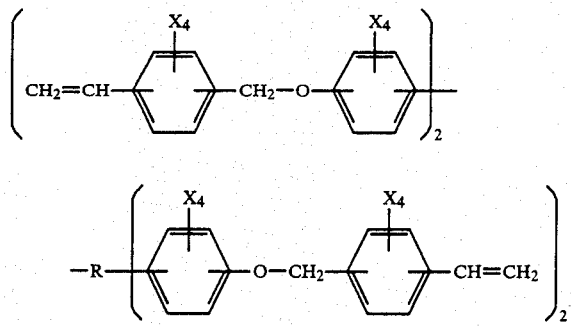

in which R is selected from the group consisting of alkyl, cycloalkyl, alkaryl and substituted alkaryl radicals and X is independently selected from the group consisting of hydrogen and halogen atoms.

2. The thermoset polymer as set forth in claim 1 in which said alkyl radical contains from 2 to about 6 carbon atoms.

3. The thermoset polymer as set forth in claim 2 in which said alkyl radical is ethylene.

4. The thermoset polymer as set forth in claim 2 in which said alkyl radical is propylene.

5. The thermoset polymer as set forth in claim 2 in which said alkyl radical is hexene.

6. The thermoset polymer as set forth in claim 1 in which said cycloalkyl radical contains from 4 to about 12 carbon atoms.

7. The thermoset polymer as set forth in claim 6 in which said cycloalkyl radical is cyclobutane.

8. The thermoset polymer as set forth in claim 6 in which said cycloalkyl radical is cyclohexane.

9. The thermoset polymer as set forth in claim 6 in which said cycloalkyl radical is cycloheptane.

10. The thermoset polymer as set forth in claim 1 in which said alkaryl radical is p-xylene.

* * * * *